United States Patent
Takahashi

[11] 4,021,663
[45] May 3, 1977

[54] AUTOMATIC EXPOSURE CONTROLLING PHOTOMETRIC DEVICE IN AN ENDOSCOPE

[76] Inventor: Nagashige Takahashi, No. 4-1, Nishi, Kokubunji, Tokyo, Japan

[22] Filed: Dec. 23, 1975

[21] Appl. No.: 643,655

[30] Foreign Application Priority Data

Dec. 26, 1974 Japan .................. 50-3927

[52] U.S. Cl. .................. 250/227; 128/4
[51] Int. Cl.² .................. G02B 5/14; H01J 5/16; H01J 39/12
[58] Field of Search .................. 250/227; 128/303.1, 128/6-9, 4

[56] References Cited
UNITED STATES PATENTS 3,599,630  8/1971  Sato et al. .................. 128/6
3,819,938  6/1974  Kornrumpf et al. .................. 250/553

Primary Examiner—Alfred E. Smith
Assistant Examiner—David K. Moore
Attorney, Agent, or Firm—Sughrue, Rothwell, Mion, Zinn & Macpeak

[57] ABSTRACT

A photosensitive device, for use in controlling the illumination intensity in an endoscope in response to the image light emerging from a fiber optical bundle in the tube of the endoscope, is positioned so as to provide only minimum interference with the image light emerging from the fiber optical bundle. A viewing lens and the photosensitive element are positioned relative to each other so that the viewing angle of incidence of the viewing lens is less than the aperture angle of the emerging light, and the photosensitive element is positioned so as to be within the aperture angle but outside of the viewing angle.

7 Claims, 2 Drawing Figures

AUTOMATIC EXPOSURE CONTROLLING PHOTOMETRIC DEVICE IN AN ENDOSCOPE

BACKGROUND OF THE INVENTION

This invention relates to a photometric device for controlling automatic exposure in an endoscope using a fibre optical system, such as optical glass fibre, and more particularly, to a photometric device which is effective to control the illumination intensity of the endoscope lamp without substantially interfering with the image light.

As is well known, an endoscope is a device having a tube which is designed for insertion into a human cavity, an objective lens at the tip of the tube, illuminating and viewing means in a housing at the opposite end of the tube, and fibre optical transmission means for carrying illuminating light from the housing to the tip and for carrying the image reflective light from the tip back to the housing for viewing by a physician or the like. Furthermore, it is known for such endoscopes to include special lights for the purpose of enabling the photographing of that part of the body being examined. Typically, if the endoscope does not include a photometric optical system for regulating the light intensity, the operator must use a camera which is provided with an automatic exposure control mechanism. In such cases, the kinds of cameras that may be used are limited because they must be provided with a photographic lens suitable for the purpose described and with an automatic exposure control mechanism. Thus, it has been extremely difficult to take a suitable photograph having the desired image magnification.

It is also known to provide, in an endoscopes of the type generally described above, a photometric device which responds to the image light intensity and controls the intensity of illumination of the flashing or illuminating lamp, whichever the endoscope is designed to use during photography. Endoscopes including a latter feature are not limited to use with automatic exposure cameras, but such endoscopes have other disadvantages. Typically, the photometric apparatus includes a beam splitting element, such as a semitransparent mirror, arranged to send a portion of the image light through the viewing lens and another portion of the image light in a direction to impinge upon the photosensitive element used in the photometric control circuitry. As a result of diverging a portion of the light to control the photosensitive element, the remaining light available for image recording is therefore reduced by 20% or more. While it would be possible to increase the amount of light available for image recording by increasing the total amount of illuminating light, the latter increase can adversely affect certain parts of the body, such as mucous membrane areas, which are being examined and photographed. Therefore, the latter expedient is not desirable. Additionally, the problem is even greater in small diameter endoscopes, such as a broncho-fiberscope which is normally only capable of transmitting an extremely small amount of light. In a latter type of endoscopes, a reduction of the quantitative light available for impinging on the film during photography by 20% or more is simply too great to be permitted.

SUMMARY OF THE INVENTION

It is therefore an object of the present invention to overcome the above disadvantages by providing a photometric arrangement in an endoscope which does not significantly reduce the amount of image light available for photographing the object.

It is another object of this invention to provide a photometric system for controlling the illumination intensity in an endoscope wherein the photosensitive element of the photometric system is positioned relative to the viewing lens such that only a minor portion of the image light impinges on the photosensitive element. These and other objects of the invention are accomplished by providing, in an endoscope, a photometric system having a photosensitive element placed within the cone of the aperture angle of the image light exiting from the fibre optical element while at the same time being outside the cone of the viewing angle of incidence determined by the viewing lens.

DETAILED DESCRIPTION OF THE INVENTION

Figure 1:
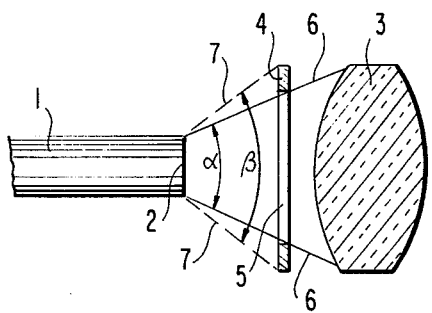
FIG. 1 is a longitudinal sectional side view of the improvement in an endoscope in accordance with the present invention.

Only the parts of the endoscope constituting the improvement herein are illustrated in the drawings. The remaining parts of the endoscope are well known to anyone of ordinary skilled in the art. As shown in the drawings, the numeral 1 represents a fibre optical bundle carrying reflected light, which has been reflected from an examined part, such as a mucous membrane, through the flexible endoscope tube towards the image light exit 2. At the image light exit 2, the image light emerges from the optical fibre at an aperture angle $\beta$ shown by dashed lines 7 in the drawings. As used herein, the aperture angle of the image light emerging from the transmission system is defined as the cone angle including substantially all of the image light emerging from the fiber optical system. A viewing lens 3 is provided in the path of the emerging light for permitting viewing, or photographing of the image. Although not shown in the drawing, it will be well understood that the endoscope further includes an illumination means for sending light via another optical fiber towards the tip of the flexible endoscope tube for the purpose of illuminating the part being examined. Furthermore, as stated previously it is known to provide a photometric system for an endoscope wherein the photosensitive element of the photometric system responds to a portion of the emerging image light to control the illumination intensity of the illuminating lamp within the endoscope.

As shown in FIG. 1, the viewing lens 3 has a viewing angle of incidence $\alpha$ determined by the angle between lines 6. The viewing angle of incidence is defined herein as the cone angle of the emerging image light which passes through the viewing lens. In the prior art it was not uncommon to have the viewing angle of incidence large enough to encompass the aperture angle of incidence. As will be apparent, such an arrangement would permit all of the emerging image light to pass through the viewing lens. However, as previously pointed out, when a photometric apparatus was used, the beam splitting element typically diverted 20% or more of the image light away from the viewing lens.

Figure 2:
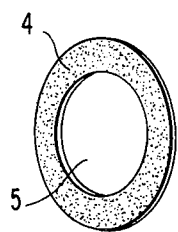
FIG. 2 is a front perspective view of the photosensitive element used in an endoscope in accordance with the present invention.

According to the present invention, the viewing lens system has an angle of incidence α which is slightly less than the aperture angle β, and the photosensitive element 4 of a photo-metric control system is positioned within the cone of the aperture angle but outside of the cone of the viewing angle of incidence. In the specific embodiment shown in FIGS. 1 and 2, the photo-sensitive element 4 is ring-shape having an opening 5. The photo-sensitive ring 4 is positioned so as to be concentric with the aperture angle and the viewing angle. The theoretical cone having an angle α passes through the opening 5 of photosensitive ring 4. The other perimeter of ring 4 is also shown in the drawing as being commensurate with the outer perimeter of the aperture cone.

The positioning of the photosensitive element as shown results in only a small portion of the total image light intensity being used for controlling the photometric apparatus whereas the greatest quantity of intensity of light is allowed to pass through the lens 3. It will be appreciated that various modifications can be made to the specific example shown in FIG. 1. For example, the viewing lens 3 could be made larger so that, in the absence of the ring 4 the viewing angle of incidence α would be as large as or larger than the aperture angle β. In such a case, the ring 4 will block light impinging thereon from the viewing lens, but the effect is the same as shown in the specific drawing of FIG. 1 because, in FIG. 1, the light impinging upon the photosensitive ring would not in any event fall on the smaller sized viewing lens. Thus, it will be apparent that the desired criteria is to select a photosensitive element which blocks only a small portion, e.g., 10 percent of the emerging image light, and a viewing lens which collects the remainder of the emerging image light.

It should be noted that the photosensitive element 4 may have its electrode in the form of a combined reflection coating and transparent electrode or a comb-tooth electrode or a corrugated electrode so as to provide an effective construction. It should further be noted in another embodiment of the invention that the photosensitive element is not limited to one having an annular shape, but a number of small elements may also be employed.

In a specific arrangement of the present invention, an image forming beam of light emitted from the light exit surface 2 of the fiber optical system 1 has an aperture angle β (for example, 60°), and the opening 5 defines a viewing angle α (for example, 40° to 50°) in conjunction with the eyepiece 3. It is known according to the characteristic of light intensity of the image light that a decrease of the viewing angle from 60° to 40° or 50° will decrease the light intensity thru the lens by no more than 10%. Thus under the conditions stated at least about 90% of the image passes thru the viewing lens. Thus, even in a small diameter endoscope such as a broncho fiberscope, an endoscopic image that may be observed for the purpose of practical use may be obtained.

Conventional devices are costly because of the requirement of high precision despite of the fact that there is employed an extremely small type beam splitter element such as a beam splitting prism or mirror, whereas the device according to the present invention may be constructed at low cost without using the beam splitting element as noted above. Further, the elimination of the beam splitting element improves the optical performance because the latter device often causes distortion of the image. In addition, according to the conventional device, when an attempt is made to utilize an eyepiece having a magnification of more than 20X, the spacing requirements for the beam splitting element and the lens necessitates a special and complicated structure, whereas, according to the present invention, such an incorporating spacing may be designed merely enough to arrange a thin photosensitive element sheet, and therefore, such element may sufficiently be incorporated using a conventional eyepiece system.

More specifically, since the present device eliminates the beam splitting element, when a camera provided with an automatic exposure control device is utilized for photographing the object being examined, effective photography may be carried out without producing loss of light due to dual photometry within the endoscope and within the camera as was the case in the prior arts.

Thus, the quantity of light from the illuminating light source may be increased or decreased, or the shutter speed of the camera may be controlled on the basis of light information sensed by the photosensitive element 4 in the device according to the present invention. In this case, despite of the fact that the quantity of light incident upon the photosensitive element 4 is relatively small, that is, about 10% or less than the image forming light, a larger light receiving area of the photosensitive element 4 peripherally arranged may be occupied, and for this reason, a relatively wide range in variation of photoconductive current may be obtained even if lesser quantity of light is received to effect the aforesaid control operation with high accuracy.

From the foregoing, it should be appreciated in the device of the invention that various disadvantages noted above with respect to the prior art photometric device in an endoscope have been overcome, and the device may obtain light conversion information required to operate an automatic exposure control device or the like with high accuracy without a substantial decrease of the quantity of light incident upon the eyepiece, and may advantageously be used particularly for a broncho fiberscope or the like having a very small diameter.

What is claimed is:

1. In an endoscope of the type having a fiber optic member forming a light transmission means and having a viewing lens spaced from an end of said fiber optic member for viewing image light emerging therefrom, and a photosensitive element for detecting variations in said image light, the improvement comprising:
   said viewing lens having a viewing angle of incidence less than the aperture angle of light emerging from the end of said fiber optic member, and said photosensitive element being positioned within said aperture angle of said image light emerging from said fiber optic member and just outside said viewing angle and facing the end of said fiber optic member from which said image light emerges.

2. The apparatus of claim 1 wherein said lens is positioned relative to the aperture angle so that the cone of the viewing angle of incidence is substantially centered within the cone of the said aperture angle, and wherein said photosensitive element surrounds at least a part of the cone of said viewing angle of incidence.

3. The apparatus of claim 2 wherein said photosensitive element is in the shape of a ring encircling the cone of said viewing angle of incidence.

4. The apparatus of claim 1 wherein the size and placement of said viewing lens is such as to cause at least 90% of said image light to be within said viewing angle of incidence.

5. The apparatus of claim 1 wherein said viewing angle of incidence is from 40° to 50° and wherein said aperture angle is about 60°.

6. The apparatus of claim 1 wherein said photosensitive element is ring shaped having an opening therein and is positioned in the path of said emerging light on the object side of said viewing lens to intercept an outer peripheral portion of the cone of said emerging light, wherein the opening of said ring shaped element determines said viewing angle of incidence.

7. The apparatus of claim 6 wherein the ring shaped element is positioned with respect to said fiber optic member such that the amount of light intercepted reduces the total intensity available for viewing by said viewing lens by no more than 10%.

* * * * *